United States Patent [19]

Quisenberry et al.

[11] Patent Number: 4,874,103
[45] Date of Patent: Oct. 17, 1989

[54] RECEPTACLE FOR RECEIVING INFECTIOUS WASTE MATERIAL

[75] Inventors: Tony M. Quisenberry, Austin; Fred E. Wahlenmeier, San Antonio, both of Tex.

[73] Assignee: Winfield Corporation, San Diego, Calif.

[21] Appl. No.: 914,111

[22] Filed: Oct. 1, 1986

[51] Int. Cl.⁴ .............................................. B65D 90/00
[52] U.S. Cl. .................................. 220/1 T; 220/254; 220/306; 206/366
[58] Field of Search ............... 220/1 T, 254, 257, 300, 220/306; 206/366; 229/43 R

[56] References Cited

U.S. PATENT DOCUMENTS

| | | |
|---|---|---|
| 619,188 | 2/1899 | Kirkwood . |
| 1,394,391 | 10/1921 | Woolsey . |
| 2,136,795 | 11/1938 | Hoffman . |
| 3,095,995 | 7/1963 | Foster . |
| 3,587,944 | 6/1971 | Pehr . |
| 3,878,067 | 4/1975 | Tremmel . |
| 4,022,352 | 5/1977 | Pehr . |
| 4,315,592 | 2/1982 | Smith . |
| 4,375,849 | 3/1983 | Hanifl . |
| 4,453,648 | 6/1984 | Harris et al. . |
| 4,488,643 | 12/1984 | Pepper . |
| 4,494,652 | 1/1985 | Nelson et al. . |
| 4,520,926 | 6/1985 | Nelson . |
| 4,552,280 | 11/1985 | Owen et al. . |
| 4,560,081 | 12/1985 | Adams . |
| 4,580,688 | 4/1986 | Harris et al. .................. 220/1 T |
| 4,585,138 | 4/1986 | Jonkers . |

*Primary Examiner*—George T. Hall
*Attorney, Agent, or Firm*—Arnold, White & Durkee

[57] ABSTRACT

A receptacle for receiving hazardous or infectious waste material which is nonreleasably sealable to prevent spillage or contamination. The receptacle includes a lower, imperforate base container for receiving and holding the waste material. A cover is provided which engages the base container in a nonreleasable fashion. The cover includes a recess having an aperture for receiving the waste material. A hinged lid is attached to the cover and includes a latch for nonreleasably securing the lid over the aperture to retain the waste material in the container. Preferably, the aperture includes a trough having converging, tapered walls to prevent spillage when the aperture is uncovered. The receptacle is made of polypropylene so that the waste material containing receptacle can be easily incinerated.

10 Claims, 3 Drawing Sheets

RECEPTACLE FOR RECEIVING INFECTIOUS WASTE MATERIAL

BACKGROUND OF THE INVENTION

1. Field of the Invention

This invention relates to a disposable waste receptacle which is particularly adapted to safely hold infectious waste material for disposal.

2. Description of the Relevant Art

In the medical field today, most hyperdermic syringes and many other medical instruments are disposable and intended for one-time use. Such disposability is desirable from the standpoint of sanitation to prevent the inadvertent transfer of communicable diseases. Particularly in view of the public attention given to such communicable diseases, it is highly desirable to take all steps possible to efficiently dispose of such medical syringes and instruments which might possibly contain infectious waste. A large number of medical infectious waste containers have been proposed, for example U.S. Pat. Nos. 4,315,592; 4,375,849; 4,494,652; and 4,560,081.

While many of such known infectious waste receptacles have desirable features, they are all somewhat deficient in the precautions taken against reuse. That is, such known infectious waste receptacles do not provide adequate protective features to prevent spillage or reopening of the receptacle after it has been filled with contaminated infectious waste material. In fact, many of such known infectious waste receptacles have features which specifically allow for easy reopening of the receptacle even after infectious waste material has been deposited.

SUMMARY OF THE INVENTION

The infectious waste receptacle of the present invention largely addresses the problems outlined above by providing a receptacle which cannot be easily reopened once the receptacle has been closed. That is, once infectious waste material is deposited within the receptacle of the present invention, a lid is shiftable into nonreleasable, locking engagement to prevent reopening or reuse of the receptacle. The locking feature thus prevents the opportunity for contamination once infectious waste material has been deposited within the receptacle. In this regard, the receptacle of the present invention represents a substantial improvement over known receptacles in that it diminishes the chance of contamination by the infectious waste material deposited.

Broadly speaking, the disposable waste receptacle hereof includes an imperforate base container for holding and receiving the infectious waste, the container having a lip around its uppermost edge. The cover overlies the edge of the base container and includes one or more pawls which engage the lip to nonreleasably lock the cover in place over the base container. Preferably, the cover includes an aperture defined by a trough having convergingly tapered walls extending into the container for receiving the infectious waste and to prevent inadvertent spillage of the waste deposited in the container. Further, the cover includes a lid which is shiftable to overly the trough. The lid has a latch mechanism which nonreleasably secures the lid overlying the trough to prevent reuse of the receptacle once the lid has been shifted into position over the trough.

In a preferred form, the cover presents a generally flat top having a recess therein. A flat shoulder is disposed in the recess, with the trough or aperture extending through the shoulder. Preferably, the shoulder includes an engagement slot extending therethrough.

The lid is connected to the top by a hinge and includes a projecting lug which is operatively receivable in the engagement slot in the shoulder. The lid and recess are cooperatively dimensioned such that with the lid shifted to overly the trough, the lid is received within the recess to adjoin the shoulder and the lug is locked in the engagement slot.

In a preferred form, the lid is hinged to the cover in the region of the shoulder, and the lid includes a large depending stud. The cover includes a socket for releasably engaging the stud. Thus, while infectious waste is being deposited through the trough into the container, the lid can be held in the open position by the engagement of the stud in the socket. In the preferred embodiments, the receptacle is made from high-density polypropylene to provide a structure which can be incinerated, and yet resistant to puncture.

DESCRIPTION OF THE PREFERRED EMBODIMENTS

Figure 1:
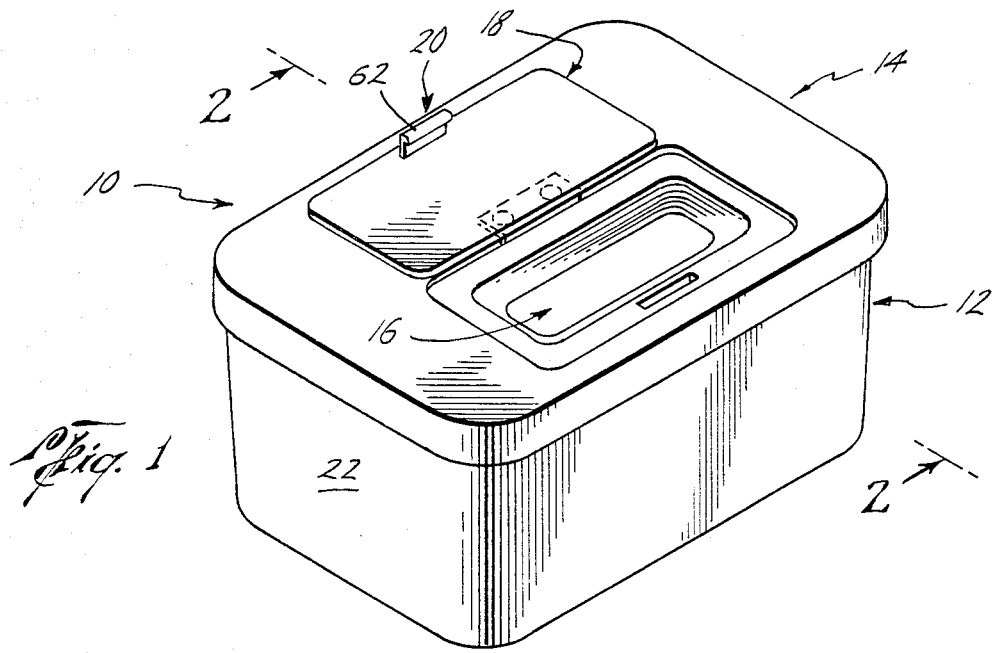
FIG. 1 illustrates a perspective view of an infectious waste receptacle in accordance with the present invention.

Turning now to the drawings, an disposable, infectious waste receptacle 10 is illustrated. Broadly speaking, the receptacle 10 includes base container 12 and cover 14 overlying the container 12. In its broad aspects, the cover 14 includes: an aperture defined by the trough 16 extending through the cover 14 for receiving the waste material; a lid 18 shiftable to a position overlying the trough; and a latch mechanism 20 for nonreleasably securing the lid overlying the trough.

Figure 2:
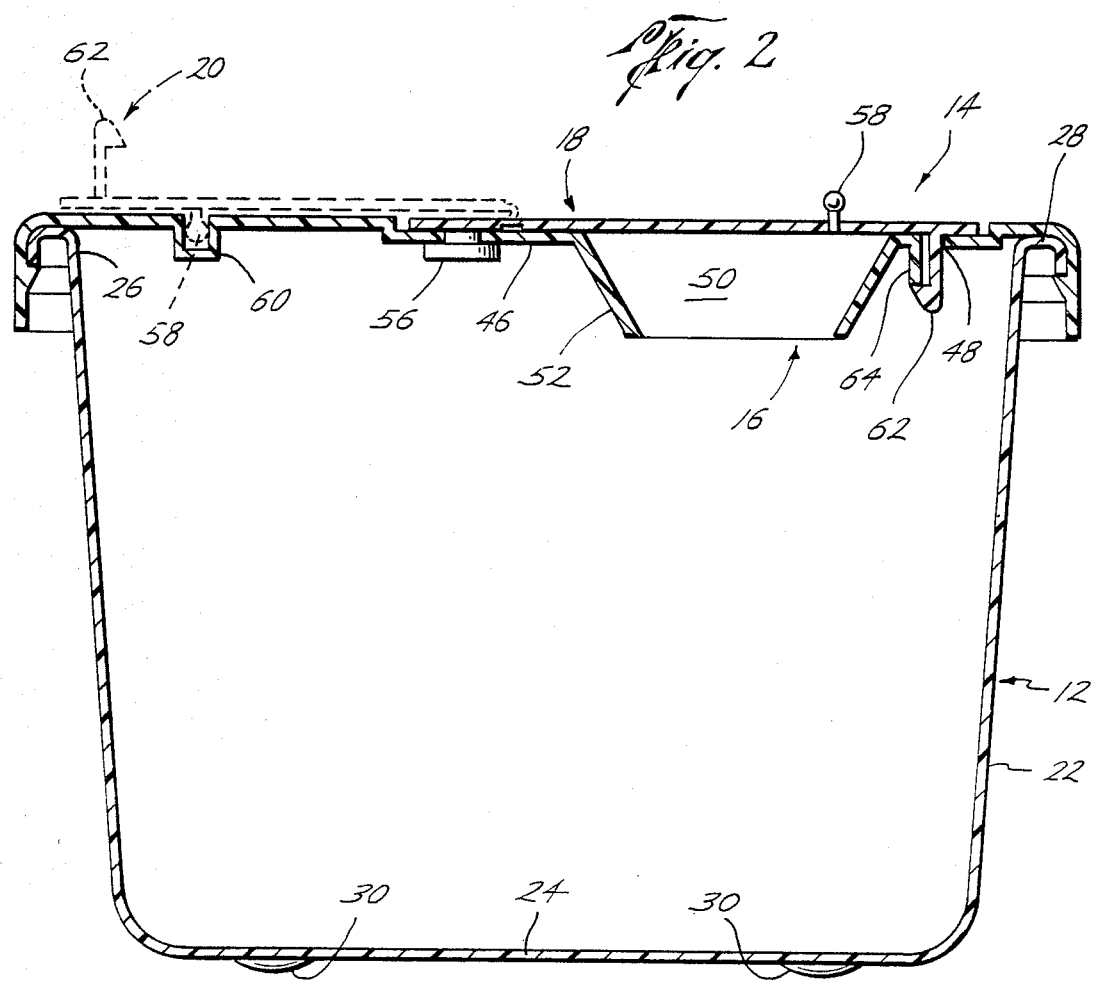
FIG. 2 is a sectional view taken along line 2—2 of FIG. 1, and shows in phantom the lid shifted into its open position.

In more detail, the container 12 is preferably made of high-density polypropylene and includes four side walls 22 and bottom 24 (see FIG. 2). A contiguous edge 26 extends along the uppermost region of the side walls 22 to define the opening into the container. The edge 26 includes lip structure 28 which, as can be seen from FIG. 2, is U-shaped in cross-section to extend outwardly from the side walls 22. Preferably, the bottom 24 includes a plurality of feet 30 which are molded during manufacture to raise the receptacle 10 slightly above any supporting surface.

Figure 3:
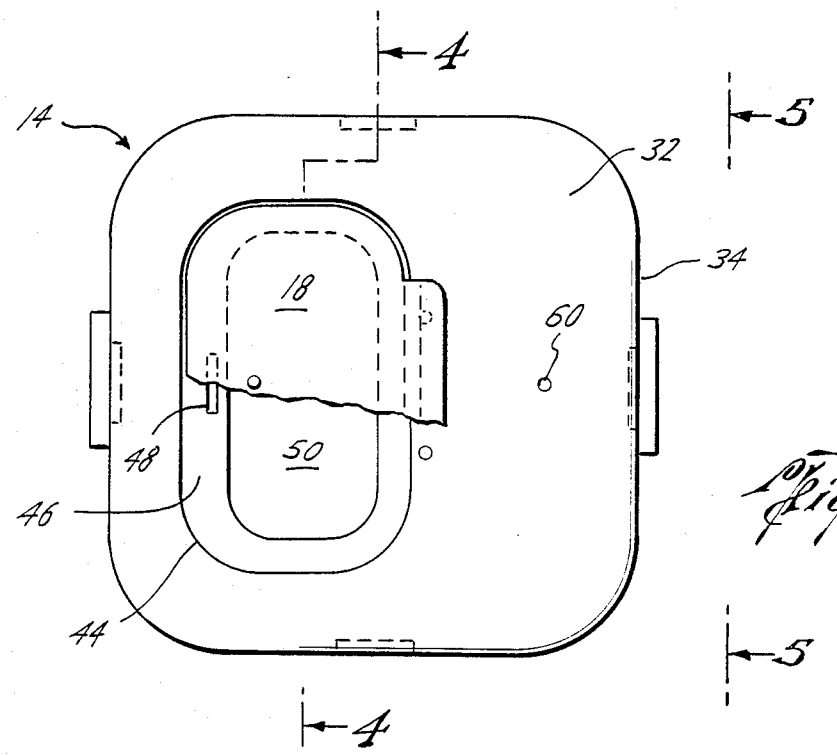
FIG. 3 is a top plan view of an alternative embodiment of the cover of the present invention with the lid shown in partial fragment for clarity.
Figure 4:
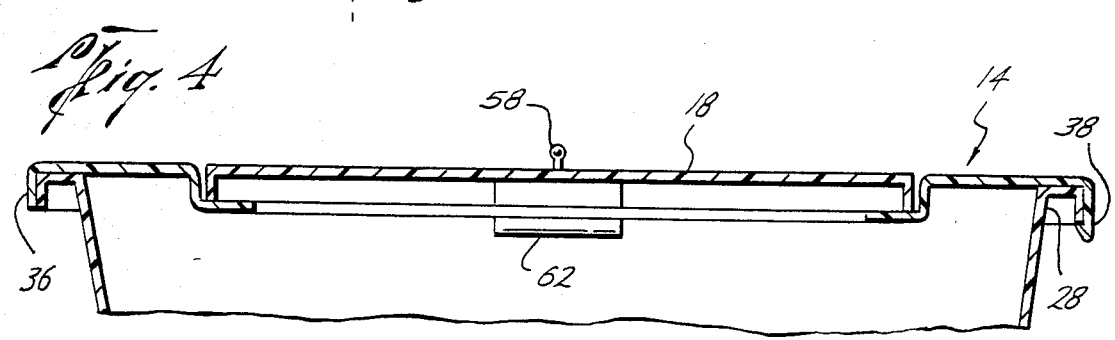
FIG. 4 is a fragmentary, sectional view along line 4—4 of FIG. 3.
Figure 5:
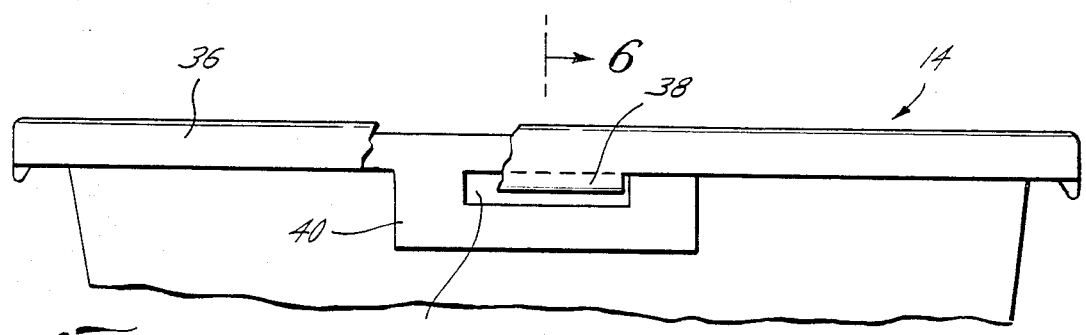
FIG. 5 is a fragmentary, side elevational view taken along line 5—5 of FIG. 3.
Figure 5:

As perhaps best seen in FIG. 3, the cover 14 includes a generally flat top 32 having an outer periphery 34. A depending flange 36 extends perpendicularly from the top 32 along the outer periphery 34 as shown in FIG. 4. At several spaced locations along the flange 36 is a pawl 38 which is operative to engage the lip 28 to nonreleasably secure the cover 14 to the base container 12. As can be seen — particularly from FIGS. 5 and 6 — the lip structure 28 includes at two locations a depending tab 40 having a groove 42 for receiving one of the pawls 38.

As shown in FIGS. 2 and 3, the cover 14 includes structure defining a recess 44 in the top 32. The recess 44 generally includes a flat shoulder 46 having an engagement slot 48 therein. In the preferred embodiments of FIGS. 1 and 2, an aperture 50 is defined by the sidewalls 52 of the contiguous trough 16, the sidewalls 52 inwardly converging to extend into the container 12. The embodiments of FIGS. 3-6 is slightly different in that the aperture 50 is generally defined by the shoulder 46 and omits the trough structure 16.

The lid 18 includes a hinge 54 to permit shiftable movement of the lid between a first position remote from the aperture 50 and a second position overlying the aperture 50. The hinge of the embodiments of FIGS. 1-6 is coupled to the shoulder region 46 of the top 32 by snaps 56 (see FIG. 2). A stud 58 depends from one side of the lid 18 (FIG. 2) and the top 32 complementally presents a socket 60. In the open position, the stud 58 is releasably received in the socket 60 to hold the lid in the first or open position.

The latch mechanism 20 generally presents a lug 62 depending from the lid 18 which is operatively receivable in the engagement slot 48. As can be seen from FIG. 2, once the lug 62 is received in the engagement slot 48, the lid 18 is secured in such a fashion that reopening of the lid 18 is difficult or impossible. In the preferred embodiment of FIG. 2, the engagement slot 48 includes a depending abutment 64 dimensioned relative to the lug 62 to secure the lid 18 in close sealing engagement to the shoulder 46.

Figure 6:
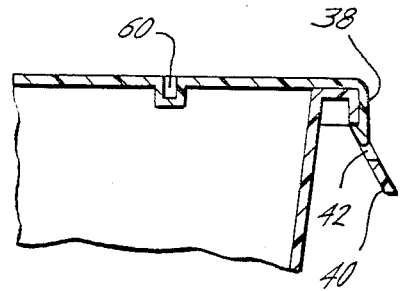
FIG. 6 is a fragmentary, sectional view taken along line 6—6 of FIG. 5 particularly illustrating the engagement of the cover with the base container.
Figure 7:
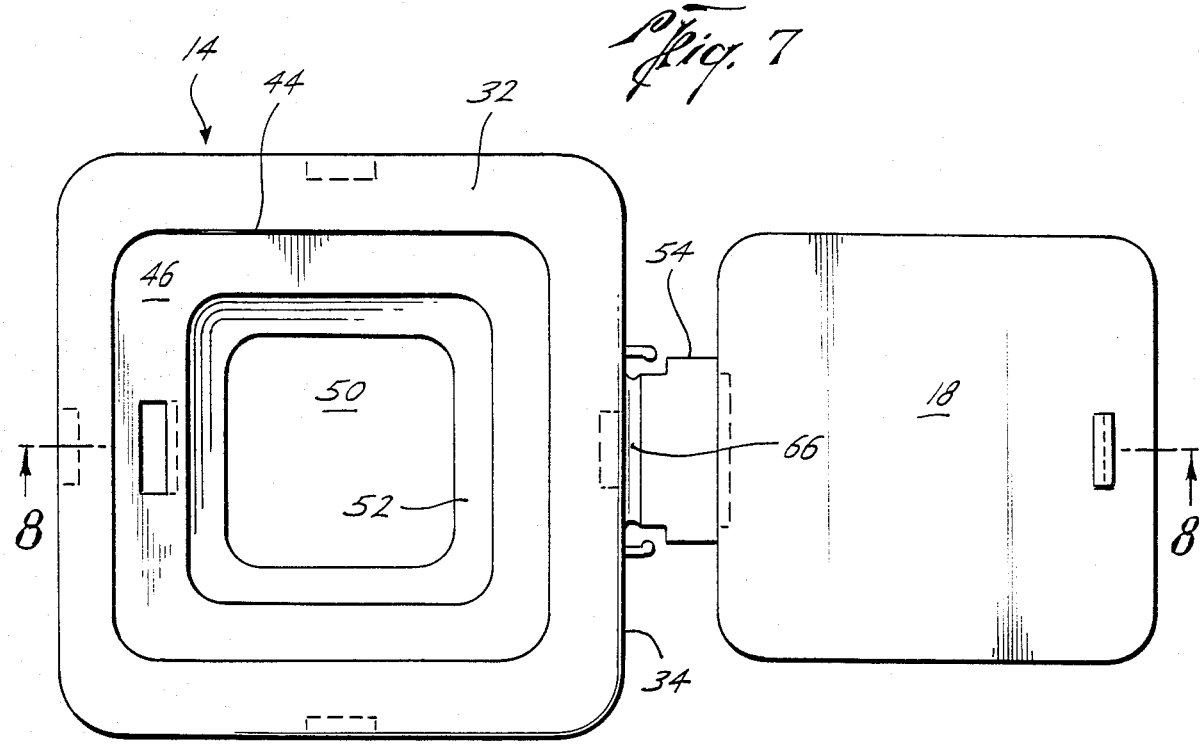
FIG. 7 is a top plan view of an other alternative embodiment of the cover of the present invention.
Figure 8:
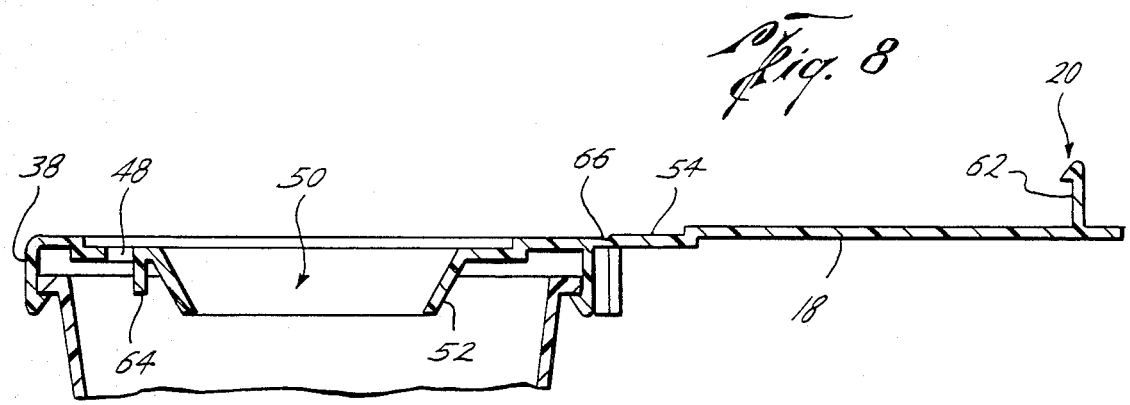
FIG. 8 is a fragmentary, sectional view of the alternative embodiment of the receptacle, taken along line 8—8 of FIG. 7.

Turning to the embodiment of FIGS. 7-8, the main differences are the dimensional features of the recess 44 and trough 52, and the hinge structure of the lid 18. As can be seen in FIG. 6, the top region 32 of the cover 14 is relatively small, with the recess 44 somewhat enlarged when compared with the embodiment of FIGS. 1-6. The shoulder region 46 is similarly somewhat enlarged, while the aperture 50 is defined by the trough 16 in similar fashion to the embodiments of FIGS. 1-2.

As can be seen in FIGS. 7 and 8, the lid 18 is attached to the outer periphery 34 of the top 32 by the hinged structure 54. The hinge structure 54 includes a thin, flexible region 66 immediately adjacent the periphery 34 so that the lid 18 can be easily shifted. As in FIGS. 1-6, the lid 18 is cooperatively dimensioned relative to the recess 44 for close reception therein.

In use, it can be readily appreciated that the dimensions of the receptacle 10 can be relatively adjusted. For example, the base container 12 might have elongated side walls 22 to present a more elongated structure when compared with the relatively low profile of the receptacle 10 illustrated in FIG. 1.

Preferably, the receptacle 10 is configured with the lid 18 in the open position as illustrated in FIG. 1 (and illustrated in phantom in FIG. 2). That is, the stud 58 is received in the socket 60 to releasably retain the lid 18 in the open position. The disposable hyperdermic syringe or other infectious waste material is deposited into the receptacle 10 by inserting the waste material through the aperture 50 into the container 12. The container 12 is substantially imperforate with the high-density polypropylene composition providing adequate safeguard against puncture by the syringe needle through the side walls 22. The trough 52 assists in depositing the waste material into the receptacle 10 and also reduces the chance of spillage and other contamination once the waste material has been deposited in the receptacle. It should be readily appreciated from the drawings that the cover 14 cannot be removed from the container 12 without destructive effort.

Once a quantity of waste material has been deposited into the receptacle 10, the lid 18 is shifted from the open position illustrated in FIG. 1, to the closed position illustrated in FIG. 3 wherein the lid 18 overlies the aperture 50. As can be seen from FIG. 2, the dimensions of the lug 62 and abutment 64 provide that the lid 18 is snug-fit against the shoulder 46. Similarly, the lid 18 (see FIG. 3) is complementally dimensioned to the recess 44 for reception therein. As can be seen in FIG. 4, with the lid 18 in a closed position, the cover 14 is generally flat, which eases handling of contaminated receptacles 10.

The operation of FIGS. 7-8 is similar, with the exception that the lid 18 is molded into the open position remote from the aperture 50. When it is desired to close the receptacle 10, the lid 18 is shifted, bending along the flexible region 66. As can be appreciated, the lug 62 of the latch mechanism 20 is inserted into the engagement slot 48 until the lug 62 catches the abutment 64 (see FIG. 8).

Once the lid 18 on the receptacle 10 has been closed, the lid 18 cannot be reopened without substantial, perhaps destructive effort. This assures that once the infectious waste material is deposited, it cannot be removed and is generally prevented from accidental contamination. In its preferred form, the entire receptacle 10 is made of polypropylene, so that the contaminated receptacle 10 can be incinerated along with the infectious waste material contained therein. Such burning of polypropylene has not been found to produce noxious or harmful gaseous by-products, allowing for safe, easy disposal of the infectious waste material along with the receptacle 10.

We claim:

1. A disposable waste receptacle comprising:
   a substantially imperforate container for holding the waste and having an edge defining an opening, the edge including a lip structure;
   a substantially flat cover overlying said opening and including pawl means for engaging said lip structure to nonreleasably lock the cover in place over the opening, the cover including:
   a generally flat top portion having an outer periphery and a recess inwardly spaced from the outer periphery;
   a substantially flat shoulder surface within the recess and generally parallel to the top portion;
   an open trough for receiving the waste and defining an open aperture extending through the shoulder with the shoulder surrounding the aperture;
   an engagement slot extending through the shoulder;
   a lid hingedly coupled to the top portion for movement between a first position remote from the aperture and a second position overlying the aperture,
   the lid having a projecting lug operatively received in the engagement slot with the lid in the second position, the lug operative to prevent return of the lid to the first position once the lug is received in the slot, the lid being cooperatively dimensioned to the recess for reception therein, such that, in the second position, the lid adjoins the shoulder surface and the cover and lid are generally flat in relation to each other.

2. The receptacle according to claim 1, wherein the lip structure includes a U-shaped flange extending along the entire edge.

3. The receptacle according to claim 1, wherein the lip structure includes a plurality of tabs, each presenting a groove for operative locking engagement with said pawl means.

4. The receptacle according to claim 1, wherein the cover includes a depending flange along its outer periphery, with the flange adjoining the edge of the container.

5. The receptacle according to claim 1, wherein the top of the cover includes a socket and the lid includes a stud for operative engagement of the stud in the socket with the lid in the first position to releasably retain the lid in the first position.

6. The receptacle according to claim 1, wherein the cover includes a hinge structure having one end coupled to the outer periphery of the top and the other end coupled to the lid.

7. The receptacle according to claim 1, wherein the cover includes a hinge structure coupling the lid to the shoulder.

8. The receptacle according to claim 1, wherein the trough includes convergingly tapered wall structure extending into the container.

9. The receptacle according to claim 1, wherein the cover comprises a polypropylene material.

10. A disposable waste receptacle comprising:
   a substantially imperforate container for holding the waste and having an edge defining an opening, the edge including a lip structure having a U-shaped flange extending along the entire edge;
   a substantially flat cover overlying said opening and including pawl means for engaging said lip structure to nonreleasably lock the cover in place over the opening, the cover including-
      a generally flat top portion having an outer periphery and a socket;
      a depending flange along the outer periphery of the top portion, with the flange adjoining the edge of the container;
      a recess in the top portion inwardly spaced from the outer periphery of the top portion;
      a substantially flat shoulder surface in the recess generally parallel to the top portion;
      an open trough extending through the shoulder surface with the shoulder surface surrounding the trough and having convergingly tapered wall structure extending into the container;
      an engagement slot extending through the shoulder surface;
   a lid hingedly coupled to the top surface for movement between a first position remote from the trough and a second position overlying the trough,
      the lid having a stud for operative engagement of the stud in the top socket with the lid in the first position to releasably retain the lid in the first position,
      the lid having a projecting lug operatively received in the engagement slot with the lid in the second position, the lug and slot operative to prevent return of the lid to the first position once the lug is received in the slot,
      the lid being cooperatively dimensioned to the recess for reception therein, such that, in the second position, the lid adjoins the shoulder surface and the cover and lid are generally flat in relation to each other.

* * * * *